US007393627B2

(12) United States Patent (10) Patent No.: US 7,393,627 B2
Ober et al. (45) Date of Patent: Jul. 1, 2008

(54) ENVIRONMENTALLY FRIENDLY PHOTOACID GENERATORS (PAGS) WITH NO PERFLUOROOCTYL SULFONATES (PFOS)

(75) Inventors: Christopher K. Ober, Ithaca, NY (US); Ramakrishnan Ayothi, Ithaca, NY (US); Kyung-Min Kim, Chungbuk (KR); Xiang-Qian Liu, Norristown, PA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 76 days.

(21) Appl. No.: 11/080,658

(22) Filed: Mar. 16, 2005

(65) Prior Publication Data

US 2005/0208420 A1 Sep. 22, 2005

Related U.S. Application Data

(60) Provisional application No. 60/553,238, filed on Mar. 16, 2004.

(51) Int. Cl.
*G03F 7/029* (2006.01)
*G03F 7/039* (2006.01)
*G03F 7/20* (2006.01)
*G03F 7/30* (2006.01)
*G03F 7/38* (2006.01)

(52) U.S. Cl. .................. 430/925; 430/921; 430/270.1; 430/325; 430/326; 430/330; 522/31

(58) Field of Classification Search ................. 430/921
See application file for complete search history.

(56) References Cited

U.S. PATENT DOCUMENTS

| 5,468,902 | A | 11/1995 | Castellanos et al. | |
| 5,514,728 | A | 5/1996 | Lamanna et al. | |
| 5,554,664 | A | 9/1996 | Lamanna et al. | |
| 5,565,500 | A | 10/1996 | Meier et al. | |
| 5,710,320 | A | 1/1998 | Vogel et al. | |
| 5,981,140 | A | 11/1999 | Sato et al. | |
| 6,200,728 | B1 | 3/2001 | Cameron et al. | |
| 6,485,883 | B2 | 11/2002 | Kodama et al. | |
| 6,692,893 | B2 | 2/2004 | Ohsawa | |
| 6,749,987 | B2* | 6/2004 | Kodama et al. | 430/270.1 |
| 6,924,323 | B2 | 8/2005 | Ishihara et al. | |
| 6,949,329 | B2* | 9/2005 | Endo et al. | 430/322 |
| 2002/0102491 | A1 | 8/2002 | Kodama et al. | |
| 2002/0197558 | A1 | 12/2002 | Ferreira et al. | |
| 2003/0027061 | A1 | 2/2003 | Cameron et al. | |
| 2003/0113658 | A1* | 6/2003 | Ebata et al. | 430/270.1 |
| 2003/0170561 | A1* | 9/2003 | Iwasawa et al. | 430/270.1 |
| 2003/0180596 | A1* | 9/2003 | Yoshimura et al. | 429/33 |
| 2003/0219679 | A1 | 11/2003 | Sasaki et al. | |
| 2004/0087690 | A1 | 5/2004 | Lamanna et al. | |

FOREIGN PATENT DOCUMENTS

| CN | 1066446 | 11/1992 |
| DE | 295421 | 10/1991 |
| EP | 1270553 A2 | 1/2003 |
| JP | 2001-159812 | 6/2001 |
| WO | WO-02/18332 A1 | 3/2002 |

OTHER PUBLICATIONS

"International Search Report for corresponding PCT Application No. PCT/U805/08678", (Mar. 3, 2006), 2 pgs.
Blotny, G., "A New, Mild Preparation of Sulfonyl Chlorides", *Tetrahedron Letters*, 44, (2003), 1499-1501.
Crivello, J. V., et al., "Diaryliodonium Salts. A New Class of Photoinitiators for Cationic Polymerization", *Macromolecules*, 10(6), (Nov.-Dec. 1977), 1307-1315.
Crivello, J. V., et al., "Synthesis and Characterization of Second-Generation Dialkylphenacylsulfonium Salt Photoinitiators", *Macromolecules*, 33(3), (2000), 825-832.
De Vleeschauwer, M., et al., "Remarkably Mild and Simple Preparations of Sulfinates, Sulfonyl Chlorides and Sulfonamides From Thioanisoles", *Synlett*, (Apr. 1997), 375-377.
Ding, Y., et al., "LnCl$_3$(cat.)/En Promoted Hydroperfluoroalkylation of α β—Unsaturated Esters With Perfluoroalkyl Iodides", *Tetrahedron Letters*, 33(52), (1992), 8119-8120.
Feiring, A. E., et al., "Aromatic Monomers With Pendant Fluoroalkylsulfonate and Sulfonimide Groups", *Journal of Fluorine Chemistry*, 105, (2000),129-135.
Feiring, A. E., "Reaction of Perfluoroalkylk Iodides With Electron Donor Nucleophiles. Addition of Perfluoroalkyl Iodides to Olefins Initiated by Electron Transfer", *Journal of Organic Chemistry*, 50(18), (1985),3269-3274.
Gisler, M., et al., "Neue Methode zur Phasentransfer-Katalysierten Sulfodechlorierung von 1-Chlor-2,4-dinitrobenzol [New Method for the Phase Transfer-Catalyzed Sulfodechlorination of 1-chloro-2,4-dinitrobenzene]", *Angewandte Chemie*, 93(2), (Abstract Only), (1981), 1 pg.
Gisler, M., et al., "Novel Method for the Phase-Transfer Catalyzed Sulfodechlorination of 1-Chloro-2,4-dinitrobenzene", *Angewandte Chemie Int. Ed. Engl.*, 20(2), (1981), 203-204.
Guo, X.-C., et al., "The First Example of Addition Reactions of Sterically Hindered Terminal Olefins, α-Substituted Styrenes, With Perfluoroalkyl Iodides Initiated by Sodium Dithionite", *Journal of Fluorine Chemistry*, 93, (1999),81-86.

(Continued)

*Primary Examiner*—Sin J. Lee
(74) *Attorney, Agent, or Firm*—Schwegman, Lundberg & Woessner P.A.

(57) ABSTRACT

Novel classes of ionic photoacid generator (PAGs) compounds having relatively environmentally friendly anions with no perfluorooctyl sulfonate (no-PFOS) are provided and photoresist composition that comprise such compounds. The new PAGs produce a photoacid having a short or no perfluoro alkyl chain (ie., no-PFOS) attached to a variety of functional groups. The PAGs of the invention are useful as photoactive component in the chemically amplified resist compositions used for microfabrication.

20 Claims, No Drawings

OTHER PUBLICATIONS

Houlihan, F. M., et al., "Design, Synthesis, Characterization, and Use of All-Organic Nonionic Photogenerators of Acids", *Chemistry of Materials*, 3(3), (1991),462-471.

Hu, C.-M., et al., "Cobaloxime-Catalyzed Hydroperfluoroalkylation of Electron-Deficient Alkenes With Perfluoroalkyl Halides: Reaction and Mechanism", *Journal of Organic Chemistry*, 57(12), (1992),3339-3342.

Hu, C.-M., et al., "Reaction of Perfluoroalkanesulfinates With Allyl and Propargy Halides. A Convenient Synthesis of 3-(Perfluoroalky)prop-1-enes and 3-(Perfluoroalkyl)allenes", *Journal of Organic Chemistry*, 56(8), (1991),2801-2804.

Hu, C.-M., et al., "Redox-Initiated Per(poly)fluoroalkylation of Olefins by Per(poly)fluoroalkyl Chlorides", *Journal of Organic Chemistry*, 56(22), (1991),6348-6351.

Imazeki, S., et al., "Facile Method for the Preparation of Triarylsulfonium Bromides Using Grignard Reagents and Chlorotrimethylsilane as an Activator", *Synthesis*, 10, (2004),1648-1654.

Iwashima, C., et al., "Synthesis of i- and g-Line Sensitive Photoacid Generators and Their Application to Photopolymer Systems", *Journal of Photopolymer Science and Technology*, 16(1), (2003),91-96.

Long, Z.-Y., et al., "The Activation of Carbon-Chlorine Bonds in Per- and Polyfluoroalkyl Chlorides: DMSO-Induced Hydroperfluoroalkylation of Alkenes and Alkynes with Sodium Dithionite", *Journal of Organic Chemistry*, 64(13), (1999),4775-4782.

Lu, X., et al., "Samarium Diiodide Initiated Addition Reaction of Fluoroalkyl Iodides to Olefins", *Tetradedron Letters*, 29(40), (1988),5129-5130.

Okamura, H., et al., "Evaluation of Quantum Yields for Decomposition of I-Line Sensitive Photoacid Generators", *Journal of Photopolymer Science and Technology*, 16(5), (2003),701-706.

Okamura, H., et al., "I-Line Sensitive Photoacid Generators and Their Use for Photocrosslinking of Polysilane/diepoxyfluorene Blend", *Journal of Photopolymer Science and Technology*, 16(1), (2003),87-90.

Okamura, H., et al., "I-Line Sensitive Photoacid Generators Having Thianthrene Skeleton", *Journal of Photopolymer Science and Technology*, 17(1), (2004),131-134.

Richard, J. P., "The Effect of β-Fluorines Substituents on the Rate and Equilibrium Constants for the Reactions of Alpha-Substituted 4-Methoxybenzyl Carbocations and on the Reactivity of a Simple Quinone Methide", *Journal of American Chemical Society*, 112(26), (1990),9513-9519.

Willenbring, R. J., et al., "New Pentafluorothio($SF_5$) Alkylsulfonic Acids", *Canadian Journal of Chemistry*, 67, (1989), 2037-2040.

Zhao, Z., "Synthesis of Sodium Picrylsulfonate", (Abstract Only), *Huaxue Shiji*, 8(5), (1986), 320 (1 pg.).

Zou, X., et al., "Synthesis of Polyfluoroalkyl-γ-lactones From Polyfluoroalkyl Halides and 4-pentenoic Acids", *Tetrahedron*, 59, (2003), 2555-2560.

\* cited by examiner

US 7,393,627 B2

ENVIRONMENTALLY FRIENDLY PHOTOACID GENERATORS (PAGS) WITH NO PERFLUOROOCTYL SULFONATES (PFOS)

CROSS-REFERENCE TO RELATED APPLICATION

This application claims the benefit, under 35 U.S.C. 119(e), of U.S. Provisional Application No. 60/553,238 filed Mar. 16, 2004, the contents of which are incorporated herein by reference.

BACKGROUND OF THE INVENTION

1. Field of the Invention

The present invention relates to new ionic photoacid generator (PAG) compounds and photoresist composition that include such compounds. In particular, the invention relates to a novel class of ionic PAGs that contain organic onium cations and new sulfonate compounds with no perfluorooctyl sulfonates (no-PFOS) anions. The new PAG anions address the combination of environmental and performance concerns raised by PFOS based PAGs.

2. Description of Related Art

Several acid catalyzed chemically amplified resist compositions have been developed. Chemically amplified resist compositions generally comprise a photosensitive acid ("photoacid") generator (PAG) and an acid sensitive polymer (resist). Upon exposure to radiation (e.g., x-ray radiation, ultraviolet radiation), the photoacid generator, by producing a proton, creates a photogenerated catalyst (usually a strong acid) during the exposure to radiation. During a post-exposure bake (PEB), the acid may act as a catalyst for further reactions. For example, the acid generated may facilitate the deprotection or cross-linking in the photoresist. The generation of acid from the PAG does not necessarily require heat. However, many known chemically amplified resists require a post-exposure bake (PEB) of one to two minutes in length to complete the reaction between the acid moiety and the acid labile component. The chemical amplification type resist materials include positive working materials that leave the unexposed material with the exposed areas removed and negative working materials that leave the exposed areas with the unexposed areas removed.

On use of the chemical amplification type, positive working, resist compositions, a resist film is formed by dissolving a resin having acid labile groups as a binder and a compound capable of generating an acid upon exposure to radiation (to be referred to as photoacid generator) in a solvent, applying the resist solution onto a substrate by a variety of methods, and evaporating off the solvent optionally by heating. The resist film is then exposed to radiation, for example, deep UV through a mask of a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally the remaining resist film is removed by dissolution in a remover solution or ashing, leaving the substrate having the desired pattern profile.

The chemical amplification type, positive working, resist compositions adapted for KrF excimer lasers generally use a phenolic resin, for example, polyhydroxystyrene in which some or all of the hydrogen atoms of phenolic hydroxyl groups are protected with acid labile protective groups. Onium salts, such as iodonium salts and sulfonium salts having perfluorinated anion, are typically used as the photoacid generator. If necessary, there are added additives, for example, a dissolution inhibiting or promoting compound in the form of a carboxylic acid and/or phenol derivative having a molecular weight of up to 3,000 in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

Ionic photoacid generators, preferably onium salts, are advantageously used as the photoacid generator in chemical amplification type resist compositions, especially chemical amplification type, positive working, resist compositions adapted for KrF excimer lasers because they provide a high sensitivity and resolution and are free from storage instability.

As stated above, photoacid generators (PAGs), play a critical role in a chemical amplified resist systems. Among the various classes of ionic and nonionic PAGs that have been developed, one of the most widely used classes is the perfluorinated onium salts. Recently, government action has made the use of the most effective PAGs based on perfluorooctyl sulfonates (PFOS), no longer viable. In addition to environmental concerns, the PFOS-based PAGs are a concern due to their fluorous self-assembly and their diffusion characteristics at smaller dimension. Previous efforts to develop new PAGs have focused mainly on improvement of the photosensitive onium cation side to increase the quantum yield or to improve the absorbance. The nature of the photoacid produced upon irradiation of the PAG is directly related to the anion of the ionic PAG. Difference in acid strength, boiling point, size, miscibility, and stability of the photoacid produced can affect the parameters related to photoresist performance, such as deprotection (or cross-linking) efficiency, photospeed, post exposure bake (PEB) sensitivity, post-exposure delay (PED) stability, resolution, standing waves, image profiles, and acid volatility. Thus, novel PAG anions that can tackle these environmental and performance issue are needed.

BRIEF SUMMARY OF THE INVENTION

The present invention focuses on the anionic part of ionic photoacid generators (PAGs). By considered design of new sulfonate anion molecule, the homogeneous distribution of the PAG in the resist is improved and appropriate mobility of the photogenerated acid is provided while at the same time addressing environmental issues. To address the environmental issues of PFOS PAGs, sulfonic acids are developed that contain far fewer than the 8 fluorinated carbons found in PFOS. A number of perfluoro segments is replaced with different functional groups that maintains the strong polarization of the acid (ie., pKa), control the size, aid film formation and compatibility with the matrix resin. In contrast to PFOS, these new PAGs with a novel fluoro-organic sulfonate anion contain many functional groups which in turn make them degrade to produce relatively short fluorine containing molecule by chemical or physical attack and are expected to be nonbioaccumalitive and environmentally friendly so that there is less impact on the environment and living organisms.

The present invention is directed to a new approach to produce environmentally friendly photoacid generators (PAGs) having anions that comprise either short or no perfluoroalkyl chain (no-PFOS) attached to a variety of functional groups. The photoacid generators of the present invention are formed from the onium salts, and derivative compounds, shown below:

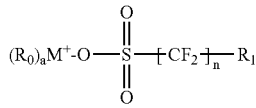
(I)

wherein, $R_1$=$CH_2CH_2CH_2OH$, $OCH_2CH_3$, $OC(CH_3)_3$, $CH_2CH_2OCH_3$, Cl, $CH_2CH_2Cl$, $CH=CH_2$, $-(CH_2)_mCH_3$, $OCF_2CF_2I$, $-CH_2CH(Br)CH_3$,

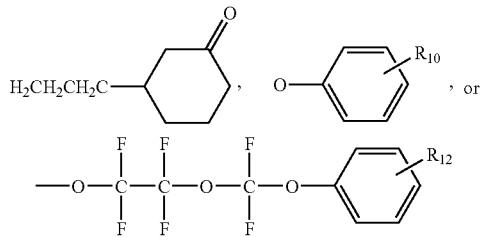

$R_{10}$=H, Br, CN, $OCH_3$, $COO^-$, $NO_2$, $OCOCH_3$
$R_{12}$=H, Br, CN, $OCH_3$, $COO^-$, $NO_2$, $OCOCH_3$
n=1 to 4 and m=1 to 15.

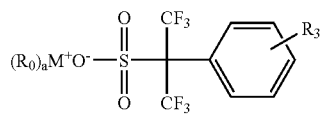
(II)

wherein $R_3$=H, F, Cl, $CH_3$

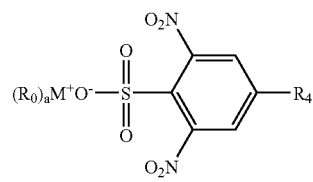
(III)

wherein, $R_4$=H, F, Br, $OCH_3$, $COO^-$, CN, $OCOCH_3$

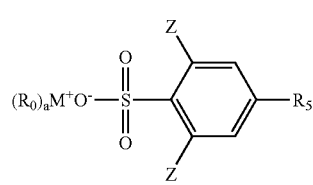
(IV)

wherein, Z=F or $CF_3$; $R_5$=H, F, $CF_3$

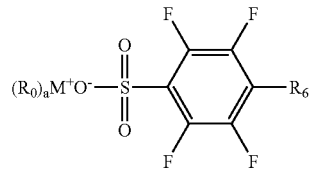
(V)

wherein $R_6$=H, F, Br, $OCH_3$, $COO^-$, CN, $OCOCH_3$

In each of the onium salt compositions provided above $R_0$ may be the same or different substituted or unsubstituted, straight, branched or cyclic alkyl group of 1 to 10 carbon atoms or substituted or unsubstituted aryl group of 6 to 14 carbon atoms, $M^+$ is any compound or atom capable of providing an onium cation, preferably a sulfur or an iodine atom, and "a" is 2 or 3, preferably "a" is equal to 3 when M is sulfur and equal to 2 when M is iodine.

The onium salts of the present invention provide a photoacid generator for chemical amplification type resist compositions comprising the onium salts defined above.

Most preferably, the invention provides a) a chemical amplification type resist composition comprising (A) a resin which changes its solubility in an alkaline developer under the action of an acid, and (B) the aforementioned photoacid generator (PAG) which generates an acid upon exposure to radiation; or b) a chemical amplification type resist composition comprising (A) a resin which changes its solubility in an alkaline developer under the action of an acid, (B) the aforementioned photoacid generator (PAG) which generates an acid upon exposure to radiation, and (C) a compound capable of generating an acid upon exposure to radiation, other than component (B). The resist composition may further include (D) a basic compound and/or (E) a carboxyl group-containing compound.

Additionally, the present invention provides a process for forming a pattern, comprising the steps of applying the aforementioned resist composition onto a substrate to form a coating; heat treating the coating and exposing the coating to high energy or electron beam through a photo-mask; optionally heat treating the exposed coating, and developing the coating with a developer.

DETAILED DESCRIPTION OF THE INVENTION

The present invention is directed to novel photoacid generators (PAGs) with no perfluorooctyl sulfonates (PFOS). The photoacid generators of the present invention are formed from onium salts, and derivative compounds, shown in Formula (I), (II), (III), (IV), and (V) below:

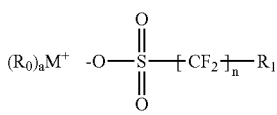
(I)

wherein, $R_1$=$CH_2CH_2CH_2OH$, $OCH_2CH_3$, $OC(CH_3)_3$, $CH_2CH_2OCH_3$, Cl, $CH_2CH_2Cl$, $CH=CH_2$, $-(CH_2)_mCH_3$, $OCF_2CF_2I$, $-CH_2CH(Br)CH_3$,

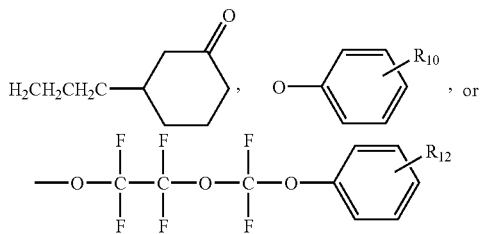

$R_{10}$=H, Br, CN, OCH$_3$, COO$^-$, NO$_2$, OCOCH$_3$
$R_{12}$=H, Br, CN, OCH$_3$, COO$^-$, NO$_2$, OCOCH$_3$
n=1 to 4 and m=1 to 15.

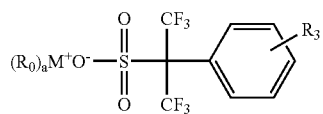 (II)

wherein R$_3$=H, F, Cl, CH$_3$

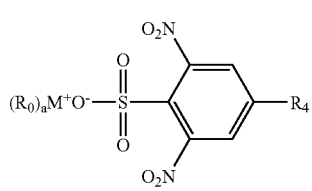 (III)

wherein, R$_4$=H, F, Br, OCH$_3$, COO$^-$, CN, OCOCH$_3$

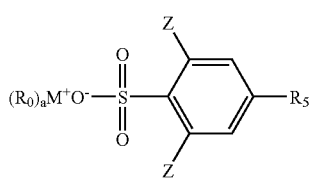 (IV)

wherein, Z=F or CF$_3$; R$_5$=H, F, CF$_3$

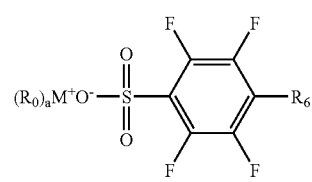 (V)

wherein R$_6$=H, F, Br, OCH$_3$, COO$^-$, CN, OCOCH$_3$

In each of the onium salt compositions provided above R$_0$ may be the same or different substituted or unsubstituted, straight, branched or cyclic alkyl group of 1 to 10 carbon atoms or substituted or unsubstituted aryl group of 6 to 14 carbon atoms, M$^+$ is any compound or atom capable of providing an onium cation, preferably a sulfur or iodine atom, and "a" is 2 or 3, preferably "a" is equal to 3 when M is sulfur and equal to 2 when M is iodine.

In formulas (I), (II), (III), (IV), and (V), M$^+$ provides an organic onium cation, most preferably M is sulfur or iodine. PAGs of the present invention contain preferably sulfonium and iodonium salt. However, other suitable organic onium salts may also be used including for example, halonium, sulfoxonium, selenonium, pyridinium, carbonium and phosphonium and certain oragnometallic complex cations (eg., Ferrocenium cations).

In formulas (I), (II), (III), (IV), and (V), R$_0$, which may be the same or different, stands for substituted or unsubstituted, straight, branched or cyclic alkyl groups of 1 to 10 carbon atoms or substituted or unsubstituted aryl groups of 6 to 14 carbon atoms. Illustrative, non-limiting, examples include straight, branched or cyclic alkyl groups such as methyl, ethyl, n-propyl, sec-propyl, n-butyl, sec-butyl, iso-butyl, tert-butyl, n-pentyl, sec-pentyl, cyclopentyl, n-hexyl, and cyclohexyl; substituted alkyl groups such as 2-oxopropyl, 2-oxocyclopentyl, 2-oxocyclohexyl, 2-hydroxycyclopentyl and 2-hydroxycyclohexyl; and aryl groups such as phenyl, 4-methylphenyl, 4-ethylphenyl, 4-methoxyphenyl, 4-tert-butylphenyl, 4-tert-butoxyphenyl, 4-cyclohexylphenyl, 4-cyclohexyloxyphenyl, 2,4-dimethylphenyl, 2,4,6-trimethylphenyl, 2,4,6-triisopropylphenyl, 3,4-bis(tert-butoxy)phenyl, 4-dimethylaminophenyl, 1-naphthyl and 2-naphthyl.

The onium salts of formula (I), (II), (III), (IV) or (V) find best use as the photoacid generator in resist materials, especially chemical amplification type resist materials although the application of the onium salts is not limited thereto. The invention provides resist compositions comprising onium salts of formula (I), (II), (III), (IV) or (V) as the photoacid generator (B). The resist compositions may be either positive or negative working. The resist compositions of the invention include a variety of embodiments, 1) a chemically amplified positive working resist composition comprising (A) a resin which changes its solubility in an alkaline developer under the action of an acid, (B) a photoacid generator comprising an onium salt of formula (I), (II), (III), (IV) or (V) capable of generating an acid upon exposure to radiation, and (G) an organic solvent;

2) a chemically amplified positive working resist composition of 1) further comprising (C) a photoacid generator capable of generating an acid upon exposure to radiation other than component (B);

3) a chemically amplified positive working resist composition of 1) or 2) further comprising (D) a basic compound;

4) a chemically amplified positive working resist composition of 1) to 3) further comprising (E) an organic acid derivative;

5) a chemically amplified positive working resist composition of 1) to 4) further comprising (F) a compound with a molecular weight of up to 3,000 which changes its solubility in an alkaline developer under the action of an acid;

6) a chemically amplified negative working resist composition comprising (B) a photoacid generator comprising an onium salt of formula (I), (II), (III), (IV) or (V) capable of generating an acid upon exposure to radiation, (H) an alkali-soluble resin, an acid crosslinking agent capable of forming a crosslinked structure under the action of an acid, and (G) an organic solvent;

7) a chemically amplified negative working resist composition of 6) further comprising (C) another photoacid generator;

8) a chemically amplified negative working resist composition of 6) or 7) further comprising (D) a basic compound; and 9) a chemically amplified negative working resist composition of 6), 7) or 8) further comprising (J) an alkali-soluble compound with a molecular weight of up to 2,500; but are not limited thereto.

Additionally, the invention provides a process for forming a pattern, comprising the steps of applying the resist composition defined above onto a substrate to form a coating; heat treating the coating and exposing the coating to high energy radiation preferably with a wavelength of up to 300 nm or electron beam through a photo-mask; optionally heat treating the exposed coating, and developing the coating with a developer.

The respective components of the resist composition are described in detail.

Component (G)

Component (G) is preferably an organic solvent. Illustrative, non-limiting, examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethylsulfoxide, γ-butyrolactone, propylene glycol methyl ether acetate, propylene glycol ethyl ether acetate, propylene glycol propyl ether acetate, methyl lactate, ethyl lactate, propyl lactate, and tetramethylene sulfone. Of these, the propylene glycol alkyl ether acetates and alkyl lactates are especially preferred.

It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture. It is also noted that the alkyl groups of the alkyl lactates are preferably those of 1 to 4 carbon atoms, for example, methyl, ethyl and propyl, with methyl and ethyl being especially preferred. These solvents may be used alone or in admixture. An exemplary useful solvent mixture is a mixture of a propylene glycol alkyl ether acetate and an alkyl lactate. The mixing ratio of the propylene glycol alkyl ether acetate and the alkyl lactate is not critical although it is preferred to mix 50 to 99 parts by weight of the propylene glycol alkyl ether acetate with 50 to 1 parts by weight of the alkyl lactate. The solvent mixture of the propylene glycol alkyl ether acetate and the alkyl lactate may further contain one or more other solvents.

Component (A)

Component (A) is a resin which changes its solubility in an alkaline developer solution under the action of an acid. It is preferably, though not limited thereto, an alkali-soluble resin having phenolic hydroxyl and/or carboxyl groups in which some or all of the phenolic hydroxyl and/or carboxyl groups are protected with acid-labile protective groups.

The preferred alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, methacrylic acid and acrylic acid. Also included are copolymers in which units free of alkali-soluble sites such as styrene, α-methylstyrene, acrylate, methacrylate, hydrogenated hydroxystyrene, maleic anhydride and maleimide are introduced in addition to the above-described units in such a proportion that the solubility in an alkaline developer may not be extremely reduced. Substituents on the acrylates and methacrylates may be any of the substituents which do not undergo acidolysis. Exemplary substituents are straight, branched or cyclic $C_{1-8}$ alkyl groups and aromatic groups such as aryl groups, but not limited thereto.

Examples of the alkali-soluble resins are given below. These polymers may also be used as the material from which the resin (A) which changes its solubility in an alkaline developer under the action of an acid is prepared and as the alkali-soluble resin which serves as component (H) to be described later. Examples include poly(p-hydroxystyrene), poly(m-hydroxystyrene), poly(4-hydroxy-2-methylstyrene), poly(4-hydroxy-3-methylstyrene), poly(α methyl-p-hydroxystyrene), partially hydrogenated p-hydroxystyrene copolymers, p-hydroxystyrene-α-methyl-p-hydroxystyrene copolymers, p-hydroxystyrene-.alpha.-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxy-styrene-methacrylic acid-methyl methacrylate copolymers, poly (methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers as well as dendritic and hyperbranched polymers thereof, but are not limited to these combinations.

The alkali-soluble resins or polymers should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by controlled free radical or living anionic polymerization.

The resin (A) is preferably an alkali-soluble resin (as mentioned above) having hydroxyl or carboxyl groups, some of which are replaced by acid labile groups such that the solubility in an alkaline developer changes as a result of severing of the acid labile groups under the action of an acid generated by the photoacid generator upon exposure to radiation.

In the chemical amplification type resist composition, an appropriate amount of (B) the photoacid generator comprising an onium salt of formula (I), (II), (III), (IV) or (V) added is from 0.5 part to 20 parts by weight, and preferably from 1 to 10 parts by weight, per 100 parts by weight of the solids in the composition. The photoacid generators may be used alone or in admixture of two or more. The transmittance of the resist film can be controlled by using a photoacid generator having a low transmittance at the exposure wavelength and adjusting the amount of the photoacid generator added.

Component (C)

In one preferred embodiment, the resist composition further contains (C) a compound capable of generating an acid upon exposure to high energy radiation, that is, a second photoacid generator other than the photoacid generator (B). The second photoacid generators include sulfonium salts and iodonium salts as well as sulfonyldiazomethane, N-sulfonyloxyimide, benzoinsulfonate, nitrobenzylsulfonate, sulfone, and glyoxime derivatives. They may be used alone or in admixture of two or more. Preferred photoacid generators used herein are sulfonium salts and iodonium salts.

In the resist composition comprising (B) the photoacid generator comprising the onium salt of formula (I), (II), (III), (IV) or (V) as the first photoacid generator according to the invention, an appropriate amount of the second photoacid generator (C) is 0 to 20 parts, and especially 1 to 10 parts by weight per 100 parts by weight of the solids in the composition. The second photoacid generators may be used alone or in admixture of two or more. The transmittance of the resist film can be controlled by using a (second) photoacid generator having a low transmittance at the exposure wavelength and adjusting the amount of the photoacid generator added.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

The basic compounds may be used alone or in admixture of two or more. The basic compound is preferably formulated in an amount of 0 to 2 parts, and especially 0.01 to 1 part by weight, per 100 parts by weight of the solids in the resist composition. The use of more than 2 parts of the basis compound would result in too low a sensitivity.

Component (E)

Illustrative examples of the organic acid derivatives (E) include, but are not limited to, organic acid derivatives including 4-hydroxyphenylacetic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxy-phenyl) valeric acid, 4-tert-butoxyphenylacetic acid, 4-(4'-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

In the resist composition comprising the onium salt according to the invention, the organic acid derivative is preferably formulated in an amount of up to 5 parts, and especially up to 1 part by weight, per 100 parts by weight of the solids in the resist composition. The use of more than 5 parts of the organic acid derivative would result in too low a resolution. Depending on the combination of the other components in the resist composition, the organic acid derivative may be omitted.

Component (F)

In one preferred embodiment, the resist composition further contains (F) a compound with a molecular weight of up to 3,000 which changes its solubility in an alkaline developer under the action of an acid, that is, a dissolution inhibitor. Typically, a compound obtained by partially or entirely substituting acid labile substituents on a phenol or carboxylic acid derivative having a molecular weight of up to 2,500 is added as the dissolution inhibitor In the resist composition comprising the onium salt according to the invention, an appropriate amount of the dissolution inhibitor (F) is up to 20 parts, and especially up to 15 parts by weight per 100 parts by weight of the solids in the composition. With more than 20 parts of the dissolution inhibitor, the resist composition becomes less heat resistant because of an increased content of monomer components.

In a chemical amplification, negative working, resist composition, (B) the photoacid generator comprising onium salts of formula (I), (II), (III), (IV) or (V) may be used as well. This composition further contains an alkali-soluble resin as component (H), examples of which are intermediates of the above-described component (A) though not limited thereto.

Examples of the alkali-soluble resin include poly(p-hydroxystyrene), poly(m-hydroxystyrene), poly(4-hydroxy-2-methylstyrene), poly(4-hydroxy-3-methylstyrene), poly($\alpha$-methyl-p-hydroxystyrene), partially hydrogenated p-hydroxystyrene copolymers, p-hydroxystyrene-$\alpha$-methyl-p-hydroxystyrene copolymers, p-hydroxystyrene-.alpha.-methylstyrene copolymers, p-hydroxystyrene-styrene copolymers, p-hydroxy-styrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers as well as dendritic and hyperbranched polymers thereof, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers, as well as dendritic and hyperbranched polymers of the foregoing polymers.

The polymer should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by controlled free radical or living anionic polymerization.

To impart a certain function, suitable substituent groups may be introduced into some of the phenolic hydroxyl and carboxyl groups on the acid labile group-protected polymer. Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isobornyl, and cyclohexyl. It is also possible to introduce acid-decomposable substituent groups such as t-butoxycarbonyl and relatively acid-undecomposable substituent groups such as t-butyl and t-butoxycarbonylmethyl.

Also contained in the negative resist composition is an acid crosslinking agent capable of forming a crosslinked structure under the action of an acid. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified, negative resist composition comprising the onium salt according to the invention. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxy-methylglycoluril, and condensates of phenolic compounds such as substituted or unsubstituted bis(hydroxymethylphenol) compounds and bisphenol A with epichlorohydrin. Especially preferred acid crosslinking agents are 1,3,5,7-tetraalkoxy-methylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine. In the resist composition, an appropriate amount of the acid crosslinking agent is about 1 to 25 parts, and especially about 5 to 15 parts by weight per 100 parts by weight of the solids in the composition. The acid crosslinking agents may be used alone or in admixture of two or more.

In the chemical amplification type, negative working, resist composition, (J) an alkali-soluble compound having a molecular weight of up to 2,500 may be blended. The compound should preferably have at least two phenol and/or carboxyl groups. Illustrative, non-limiting, examples include cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl) valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more. The addition amount is 0 to 20 parts, preferably 2 to 10 parts by weight per 100 parts by weight of the solids in the composition although it is not critical.

In the resist composition according to the invention, there may be added such additives as a surfactant for improving coating, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products K.K.), Megaface F171, F172 and F173 (Dai-Nippon Ink & Chemicals K.K.), Florade FC430 and FC431 (Sumitomo 3M K.K.), Asahiguard AG710, Surflon S-381, S-382, SC101, SC102, SC103, SC104, SC105, SC106, Surfynol E1004, KH-10, KH-20, KH-30 and KH-40 (Asahi Glass K.K.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo K.K.). Inter alia, FC430, Surflon S-381 and Surfynol E1004 are preferred. These surfactants may be used alone or in admixture.

In the resist composition according to the invention, the surfactant is preferably formulated in an amount of up to 2 parts, and especially up to 1 part by weight, per 100 parts by weight of the solids in the resist composition.

In the resist composition according to the invention, a UV absorber may be added. An appropriate amount of UV absorber blended is 0 to 10 parts, more preferably 0.5 to 10 parts, most preferably 1 to 5 parts by weight per 100 parts by weight of the base resin.

For the microfabrication of integrated circuits, any well-known lithography may be used to form a resist pattern from the chemical amplification, positive or negative working, resist composition according to the invention.

The composition is applied onto a substrate (e.g., Si, SiO.sub.2, SiN, SiON, TiN, WSi, BPSG, SOG, organic anti-reflecting film, etc.) by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 120° C. for 1 to 5 minutes. The resulting resist film is generally 0.1 to 2.0 µm thick. With a mask having a desired pattern placed above the resist film, the resist film is then exposed to actinic radiation, preferably having an exposure wavelength of up to 300 nm, such as UV, deep-UV, electron beams, x-rays, excimer laser light, γ-rays and synchrotron radiation in an exposure dose of about 1 to 200 mJ/cm$^2$, preferably about 10 to 100 mJ/cm$^2$. The film is further baked on a hot plate at 60 to 150° C. for 1 to 5 minutes, preferably 80 to 120° C. for 1 to 3 minutes (post-exposure baking=PEB).

Thereafter the resist film is developed with a developer in the form of an aqueous base solution, for example, 0.1 to 5%, preferably 2 to 3% aqueous solution of tetramethylammonium hydroxide (TMAH) for 0.1 to 3 minutes, preferably 0.5 to 2 minutes by conventional techniques such as dipping, puddling or spraying. In this way, a desired resist pattern is formed on the substrate. It is appreciated that the resist composition of the invention is best suited for micro-patterning using such actinic radiation as deep UV with a wavelength of 254 to 193 nm, 13.4 nm (EUV), electron beams, x-rays, excimer laser light, γ-rays and synchrotron radiation. With any of the above-described parameters outside the above-described range, the process may sometimes fail to produce the desired pattern.

EXAMPLES

The onium salts may be synthesized using known methods and techniques. The following are several examples of preferred embodiments of the onium salts in accordance with the present invention. However, the synthesis methods and techniques are not limited by the following examples.

A typical synthetic procedure to obtain an onium salt as depicted in Formula (VI) carrying short perfluoroalkyl chain as counter ion is described below.

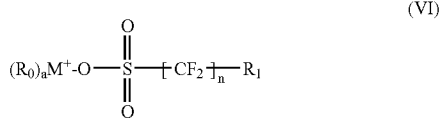

(VI)

wherein M is I or S, a=2 when M is I and a=3 when M is S, n = 1 to 4, $R_0$ is $C_6H_5$, and $R_1$ = $(CH_2)_6CH_3$, $(CH_2)_7CH_3$, $OCH_2CH_3$,

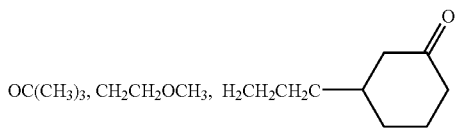

$OC(CH_3)_3$, $CH_2CH_2OCH_3$, $H_2CH_2CH_2C-$

Iodochlorotetrafluoroalkane was transformed to sodium chlorotetrafluoroalkane sulfinate on reaction with sodium dithionite and sodium bicarbonate in aqueous acetonitrile. The sulfinate reacted smoothly with elemental chlorine in water at 0° C. and gave sulfonyl chloride, which in turn was converted to its sulfonate using sodium hydroxide as the oxidizing agent. Alkylated perfluoroalkane sulfonate was obtained either by addition of sulfonate to an olefin in the presence of ammonium persulfate $[(NH_4)_2S_2O_8]$ or by reacting metal alkoxide with sulfonate. The alkylated perfluoralkane sulfonate underwent an exchange reaction with photosensitive cation in methanol or $CH_2Cl_2/H_2O$ or ketonic solvents and produces a new ionic photoacid generator.

Synthetic procedure to attain the onium salts of Formula (VII), Formula (X), and Formula (VIII), carrying short perfluoroalkyl chain as counter ion is summarized below.

(VII)

(X)

(VIII)

wherein M is I or S, a=2 when M is I and a=3 when M is S, n=2, m=2 or 4, $R_0$ is $C_6H_5$, $R_2$=Cl, $CH_2CH_2OH$, $CH_2CH_2CH_2OH$, $CH_2CH_2Cl$, $CH=CH_2$, and $R_3$=$CH_2CH(Br)CH_3$ Bromo(or iodo) tetrafluoralkane was transformed to sodium perfluoroalkane sulfinate on reaction with sodium dithionite and sodium bicarbonate in aqueous acetonitrile. The sulfinate reacted smoothly with elemental chlorine in water at 0° C. and gave sulfonyl chloride, which in turn was converted to its sulfonate using ammonium hydroxide as the oxidizing agent. The perfluoralkane sulfonate underwent an exchange reaction with photosensitive cation in methanol or $CH_2Cl_2/H_2O$ or ketonic solvents and produces a new ionic photoacid generator.

Synthetic route to obtain the onium salt of Formula (IX) carrying short perfluoroether chain as counter ion discussed below.

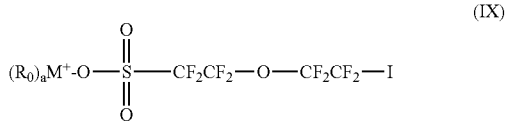

(IX)

wherein M is I or S, a=2 when M is I and a=3 when M is S, and $R_0$ is $C_6H_5$

5-Iodooctafluoro-3-oxapentanesulphonyl fluoride was transformed to its lithium sulfonate using lithium carbonate as the oxidizing agent. The perfluorether sulfonate underwent an exchange reaction with photosensitive cation in methanol or $CH_2Cl_2/H_2O$ or ketonic solvents and produces a new ionic photoacid generator.

The synthetic procedure to arrive at an anionic part of the onium salt of Formula (XI) and Formula (XII) with perfluoroalkyl group or perfluoroether which in turn attached to phenyl/substituted phenyl group via an ether linkage is summarized below.

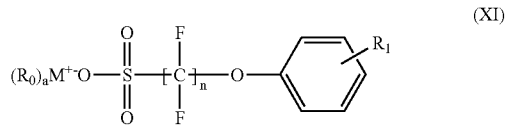

(XI)

wherein M is I or S, a=2 when M is I and a=3 when M is S, n=1 to 4,

R$_0$ is C$_6$H$_5$, and R$_1$=H, Br, CN, OCH$_3$, COO$^-$, NO$_2$, OCOCH$_3$

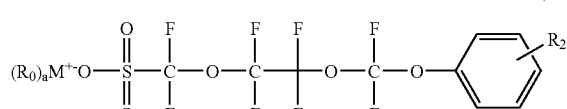
(XII)

wherein M is I or S, a=2 when M is I and a=3 when M is S

R$_0$ is C$_6$H$_5$, and R$_2$=H, Br, CN, OCH$_3$, COO$^-$, NO$_2$, OCOCH$_3$

Reaction of potassium salt of phenol with dihalotetrafluoroalkane or with 1,6-dibromoperfluoro-2,5-dioxahexane results in phenyl ether which is transformed to sulfinate on reaction with sodium dithionite and sodium bicarbonate in aqueous acetonitrile. The sulfinate can be converted to sulfonate by two methods either by reacting the sulfinate with elemental chlorine in water to sulfonyl chloride then oxidation with lithium hydroxide in aqueous THF or direct oxidation with hydrogen peroxide in aqueous acetonitrile. Finally an exchange reaction of sulfonate with photoactive cation in aqueous acetonitrile or ketonic solvents such as acetone, 2-butanone or 4-methyl-2-pentanone affords a new ionic photoacid generator.

A typical synthetic procedure to obtain an anionic part of the onium salt of Formula (XIII) with branched perfluoroalkyl group which in turn attached to phenyl/substituted phenyl group is described below.

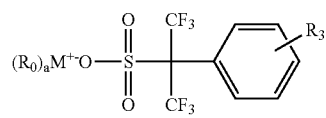
(XIII)

wherein M is I or S, a=2 when M is I and a=3 when M is S,

R$_0$ is C$_6$H$_5$, and R$_3$=H, F, Cl, CH$_3$

Reaction of hexafluoro-2-phenylisopropanol or the substituted phenyl version with phosphorus tribromide results in hexafluoro-2-phenylisopropyl bromide which can be transformed to sulfinate on reaction with sodium dithionite and sodium bicarbonate in aqueous acetonitrile. The sulfinate can be converted to sulfonate by two methods either by reacting the sulfinate with elemental chlorine in water to sulfonyl chloride then oxidation with lithium hydroxide in aqueous THF or direct oxidation with hydrogen peroxide in aqueous acetonitrile. Finally an exchange reaction of sulfonate with photoactive cation in aqueous acetonitrile or ketonic solvents such as acetone, 2-butanone or 4-methyl-2-pentanone affords a new ionic photoacid generator.

A simplified synthetic procedure to arrive an anionic part of the onium salt of Formula (XIV), Formula (XV), and Formula (XVI) with phenyl ring directly attached to the sulfonium ions is described below.

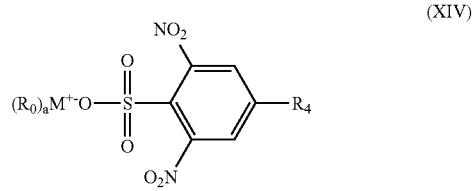
(XIV)

wherein M is I or S, a=2 when M is I and a=3 when M is S, R$_0$ is C$_6$H$_5$, and R$_4$=H, F, Br, OCH$_3$, COO$^-$, CN, OCOCH$_3$

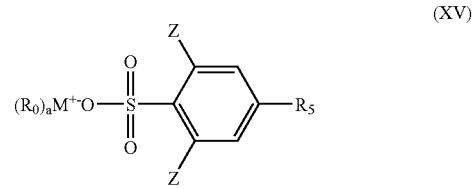
(XV)

wherein M is I or S, a=2 when M is I and a=3 when M is S, R$_0$ is C$_6$H$_5$, Z=F or CF$_3$, and R$_5$=H, F, CF$_3$

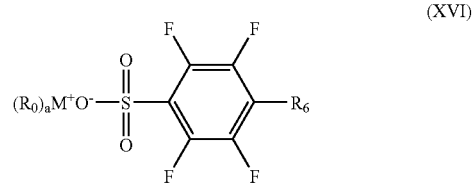
(XVI)

wherein M is I or S, a=2 when M is I and a=3 when M is S R$_0$ is C$_6$H$_5$, and R$_6$=H, F, Br, OCH$_3$, COO$^-$, CN, OCOCH$_3$ The sulfonate can be synthesized either by direct sulfodehalogenation reaction or from the sulfonic acid by treating with silver or lithium or sodium compounds. Reaction of aromatic halogen with sodium hydrogen sulfite or sodium sulfate or potassium metabisulfite can result corresponding sulfonate. Finally an exchange reaction of sulfonate with photoactive cation in aqueous acetonitrile or ketonic solvents such as acetone, 2-butanone or 4-methyl-2-pentanone affords a new ionic photoacid generator.

Although the present invention has been disclosed in terms of a preferred embodiment, it will be understood that numerous additional modifications and variations could be made thereto without departing from the scope of the invention as defined by the following claims.

We claim:

1. A photoacid generator for a chemical amplification type resist composition comprising an onium salt of formula (IX):

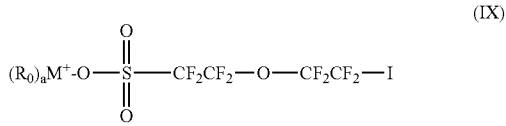
(IX)

wherein, M is a sulfur or iodine atom, and "a" is equal to 3 when M is sulfur and equal to 2 when M is iodine, and $R_0$ is $C_6H_5$.

2. A chemical amplification type resist composition comprising,
   a) a resin which changes its solubility in an alkaline developer under the action of an acid, and
   b) the photoacid generator of claim 1 which generates an acid upon exposure to radiation.

3. A process for forming a pattern, comprising
   a) applying the resist composition of claim 2 onto a substrate to form a coating;
   b) heat treating the coating and exposing the coating to high energy radiation or electron beam through a photomask; and
   c) optionally heat treating the exposed coating, and developing the coating with a developer.

4. The photoacid generator of claim 1 wherein M is a sulfur atom, "a" is 3, and $R_0$ is $C_6H_5$.

5. The photoacid generator of claim 1 wherein M is an iodine atom, "a" is 2, and $R_0$ is $C_6H_5$.

6. A photoacid generator for a chemical amplification type resist composition comprising an onium salt of formula (X):

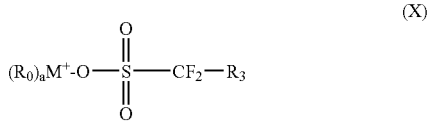

wherein, M is a sulfur or iodine atom, and "a" is equal to 3 when M is sulfur and equal to 2 when M is iodine, $R_0$ is $C_6H_5$ and $R_3 = CH_2CH(Br)CH_3$.

7. A chemical amplification type resist composition comprising,
   a) a resin which changes its solubility in an alkaline developer under the action of an acid, and
   b) the photoacid generator of claim 6 which generates an acid upon exposure to radiation.

8. A process for forming a pattern, comprising
   a) applying the resist composition of claim 7 onto a substrate to form a coating;
   b) heat treating the coating and exposing the coating to high energy radiation or electron beam through a photomask; and
   c) optionally heat treating the exposed coating, and developing the coating with a developer.

9. The photoacid generator of claim 6 wherein M is a sulfur atom, "a" is 3, $R_0$ is $C_6H_5$, and $R_3$ is $-CH_2CH(Br)CH_3$.

10. The photoacid generator of claim 6 wherein M is an iodine atom, "a" is 2, $R_0$ is $C_6H_5$, and $R_3$ is $-CH_2CH(Br)CH_3$.

11. A photoacid generator for a chemical amplification type resist composition comprising an onium salt of formula (XI):

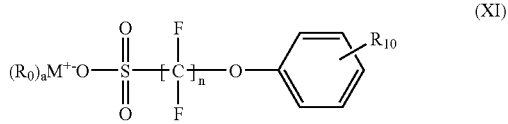

wherein, M is a sulfur or iodine atom, and "a" is equal to 3 when M is sulfur and equal to 2 when M is iodine, $R_0$ is $C_6H_5$, n=1 to 4, and $R_{10}$=H, Br, CN, $OCH_3$, $COO^-$, $NO_2$, or $OCOCH_3$.

12. A chemical amplification type resist composition comprising,
   a) a resin which changes its solubility in an alkaline developer under the action of an acid, and
   b) the photoacid generator of claim 11 which generates an acid upon exposure to radiation.

13. A process for forming a pattern, comprising
   a) applying the resist composition of claim 12 onto a substrate to form a coating;
   b) heat treating the coating and exposing the coating to high energy radiation or electron beam through a photomask; and
   c) optionally heat treating the exposed coating, and developing the coating with a developer.

14. The photoacid generator of claim 11 wherein, M is a sulfur atom, "a" is 3, $R_0$ is $C_6H_5$, n is 1-4, and $R_{10}$ is H, Br, CN, $OCH_3$, $COO^-$, $NO_2$, or $OCOCH_3$.

15. The photoacid generator of claim 11 wherein, M is an iodine atom, "a" is 2, $R_0$ is $C_6H_5$, n is 1-4, and $R_{10}$=H, Br, CN, $OCH_3$, $COO^-$, $NO_2$, or $OCOCH_3$.

16. A photoacid generator for a chemical amplification type resist composition comprising an onium salt of formula (XII):

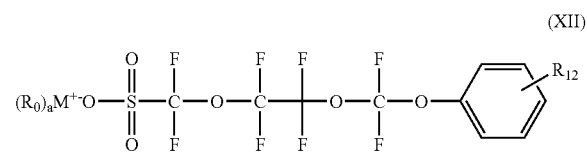

wherein, M is a sulfur or iodine atom, and "a" is equal to 3 when M is sulfur and equal to 2 when M is iodine, $R_0$ is $C_6H_5$, and $R_{12}$=H, Br, CN, $OCH_3$, $COO^-$, $NO_2$, or $OCOCH_3$.

17. A chemical amplification type resist composition comprising,
   a) a resin which changes its solubility in an alkaline developer under the action of an acid, and
   b) the photoacid generator of claim 16 which generates an acid upon exposure to radiation.

18. A process for forming a pattern, comprising:
   a) applying the resist composition of claim 17 onto a substrate to form a coating;
   b) heat treating the coating and exposing the coating to high energy radiation or electron beam through a photomask; and
   c) optionally heat treating the exposed coating, and developing the coating with a developer.

19. The photoacid generator of claim 16 wherein, M is a sulfur atom, and "a" is 3, $R_0$ is $C_6H_5$, and $R_{12}$ is H, Br, CN, $OCH_3$, $COO^-$, $NO_2$, or $OCOCH_3$.

20. The photoacid generator of claim 16 wherein, M is an iodine atom, and "a" is 2, $R_0$ is $C_6H_5$, and $R_{12}$ is H, Br, CN, $OCH_3$, $COO^-$, $NO_2$, or $OCOCH_3$.

* * * * *